US00PP23851P2

(12) United States Plant Patent
van Zoest

(10) Patent No.: US PP23,851 P2
(45) Date of Patent: Aug. 27, 2013

(54) ***CLEMATIS* PLANT NAMED 'ZOBADOL'**

(50) Latin Name: ***Clematis* hybrid**
Varietal Denomination: Zobadol

(75) Inventor: Jan van Zoest, Boskoop (NL)

(73) Assignee: J. Van Zoest Beheer B.V., Boskoop (NL)

( * ) Notice: Subject to any disclaimer, the term of this patent is extended or adjusted under 35 U.S.C. 154(b) by 70 days.

(21) Appl. No.: 13/385,252

(22) Filed: Feb. 10, 2012

(51) Int. Cl.
*A01H 5/00* (2006.01)

(52) U.S. Cl.
USPC ..... Plt./228

(58) Field of Classification Search
USPC ..... Plt./228
See application file for complete search history.

*Primary Examiner* — Annette Para
(74) *Attorney, Agent, or Firm* — Penny J. Aguirre

(57) ABSTRACT

A new cultivar of hybrid *Clematis*, 'Zobadol', characterized by its upright flowers that are pale violet in color, its blooming ability in spring and even more abundantly in summer, its flowers that retain their color with very little fading, its near sterility, and its cold hardiness to at least U.S.D.A. Zone 6.

2 Drawing Sheets

Botanical classification: *Clematis* hybrid.
Variety denomination: 'Zobadol'.

CROSS REFERENCE TO A RELATED APPLICATION

This application is co-pending with a U.S. Plant Patent Application filed for a plant derived from similar parentage that is entitled *Clematis* Plant Named 'Zobast' (U.S. Plant patent application Ser. No. 13/385,272).

BACKGROUND OF THE INVENTION

The present invention relates to a new and distinct cultivar of *Clematis*, botanically an interspecific hybrid, and will be referred to hereafter by its cultivar name 'Zobadol'. 'Zobadol' is grown as an herbaceous climbing plant for use in the landscape or as a flowering potted plant for the terrace.

'Zobadol' derived from an ongoing breeding program by the inventor in his nursery in Boskoop, The Netherlands. The goal of the selection was to select a hardy climber with a dwarf habitus that could be grown for different purposes in the garden.

'Zobadol' arose as a seedling derived from open pollination of an unnamed plant from the breeding program, designated as No. 19960074 in 2003. 'Zobadol' was selected as a single unique plant from the batch of seedlings in 2006.

'Zobadol' was selected in 2006 and arose from open pollinated seed from *Clematis* 19960074, unpatented. The seed was selected in 2003, the seedling 'Zobadol' was selected from the batch of seedlings in 2006. The new cultivar primarily differs from the seed plant by its extreme floriferous habitus and flower color.

Asexual reproduction of the new cultivar was first accomplished by internodial stem cuttings under the direction of the inventor in Boskoop, The Netherlands in 2006. The characteristics of this cultivar have been determined to be stable and are reproduced true to type in successive generations.

SUMMARY OF THE INVENTION

The following traits have been repeatedly observed and represent the characteristics of the new cultivar as grown outdoors and observed for five years in Boskoop, The Netherlands. These attributes in combination distinguish 'Zobadol' from other varieties of *Clematis* known to the inventor.

1. 'Zobadol' exhibits upright flowers that are pale violet in color.
2. 'Zobadol' blooms in spring and even more abundantly in summer.
3. 'Zobadol' has flowers that fade very little.
4. 'Zobadol' is more or less sterile, seed is rarely produced.
5. 'Zobadol' is cold hardy to at least U.S.D.A. Zone 6.

'Zobadol' differs from its female parent, No. 19960074, in having pale violet to white flowers rather then violet-blue, and in its extreme floriferous habitus. 'Zobast' differs from 'Zobadol' in having white flowers and in occasionally having double flowers.

'Zobadol' can be most closely compared to the cultivars 'Yukikomachi' (not patented) and 'Ivan Olsson' (not patented), differences are described in TABLE 1.

TABLE 1

| | Characteristic | Description | 'Zobadol' |
|---|---|---|---|
| 'Yukikomachi' | Tepal shape | Usually overlapping at the base | Usually not overlapping at the base |
| 'Yukikomachi' | Tepal color on upper surface | White with just a bit violet tint | Pale violet with paler center |
| 'Ivan Olsson' | Color of the anther | Dark purple | Yellow |

BRIEF DESCRIPTION OF THE DRAWING

The accompanying colored photographs illustrate the overall appearance and distinct characteristics of the new *Clematis*. The photographs were taken of a three year-old plant of 'Zobadol' as grown in a one-gallon container in Boskoop, The Netherlands.

The photograph in FIG. 1 shows the flowering habitus.

Figure 1:
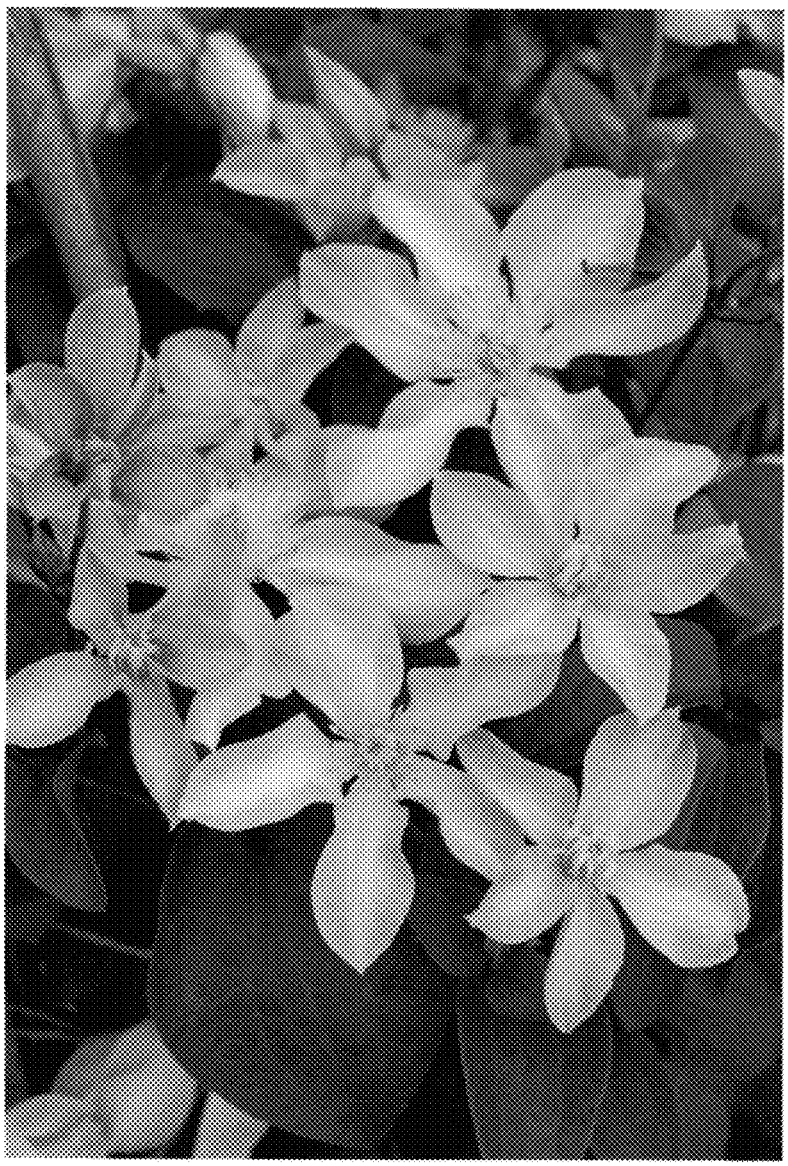
Figure 2:
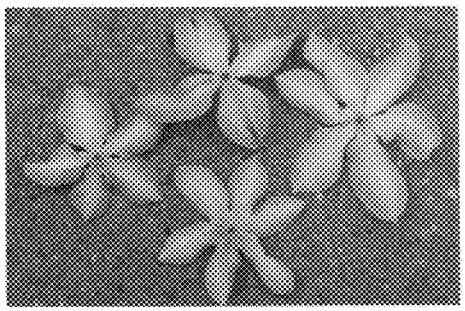

The photograph in FIG. 2 shows the back of the flower.

Figure 3:
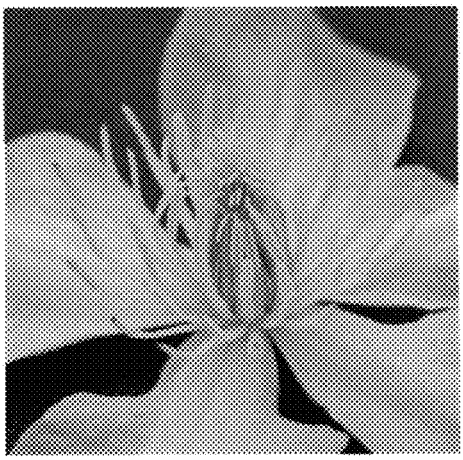

The photograph in FIG. 3 shows the inside of the flower with a close-up view of the stamens and pistils.

Figure 4:
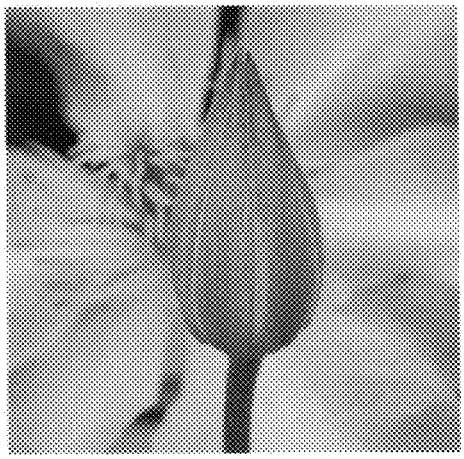

The photograph in FIG. 4 shows the flower bud.

Figure 5:
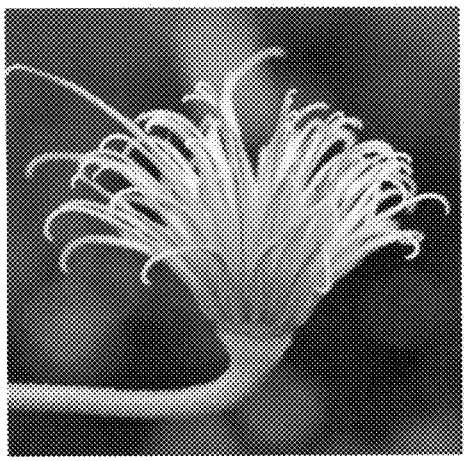
Figure 6:
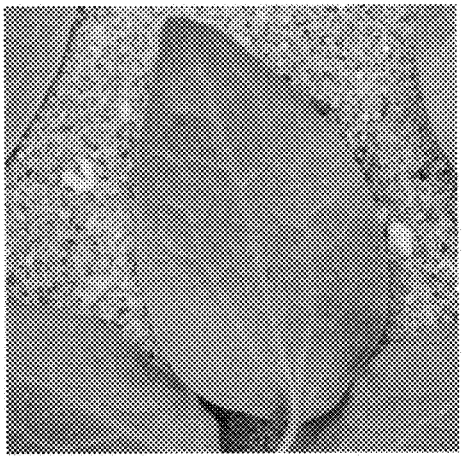

The photograph in FIG. 5 shows the seedhead and the photograph in FIG. 6 shows the lower surface of the leaves. The colors of the photographs are as close as possible with the digital photography techniques available, the color values cited in the detailed botanical description describe the colors as accurately as possible of the new *Clematis*.

DETAILED BOTANICAL DESCRIPTION

The following is a detailed description of three year-old plants of *Clematis* 'Zobadol' as grown outdoors in one-gallon containers under full sun at a nursery in Boskoop, The Netherlands. The phenotype of the new cultivar *Clematis* may vary with variations in environmental, climatic and cultural conditions as the cultivar has not been tested under all possible environmental conditions. The color determination is in accordance with The 2001 R.H.S. Color Chart, London, England, except where general color terms of ordinary dictionary significance are used.

General description:

*Botanical classification.*—*Clematis* 'Zobadol'(classified in the Patens Group).

*Blooming period.*—Blooms for 4 to 6 weeks in spring and more abundantly in summer for 6 to 8 weeks.

*Plant habit.*—Herbaceous climber.

*Height and spread.*—Three year-old plant is about 15 cm at the base with a height of about 1.5 m height when pruned after the first flowering.

*Cold hardiness.*—At least to U.S.D.A. Zone 6.

*Culture.*—Moist but well-drained soil in full sun with the roots shaded.

*Diseases and pests.*—No resistance to wilt had been observed.

*Root description.*—Fleshy.

Growth and propagation:

*Propagation.*—Internodial soft wood cuttings from vegetative shoots.

*Root initiation.*—Roots develop in 6 weeks in summer under greenhouse conditions.

*Time required for root development.*—75 to 90 days to develop a 5-cm container from a 5-cm cutting.

*Growth rate.*—Moderately vigorous once planted out.

Stem description:

*Shape.*—Round and 6 ribbed.

*Stem color.*—175A on upper surface, 166B on lower surface.

*Stem size.*—About 1.5 m (including peduncle and terminal pedicel) in length, an average of 2 to 3 mm in diameter.

*Stem surface.*—Sparsely hairy, but more densely so near the nodes.

*Internode length.*—Ranges from 6 to 10 cm.

*Branching.*—Basal branches.

Foliage description:

*Leaf arrangement.*—Opposite.

*Leaf division.*—Simple or ternate.

*Leaf size.*—Up to 10 cm long and 9 cm in width.

*Leaf attachment.*—Petiolate.

*Leaflet shape.*—Ovate, elliptic.

*Leaflet base.*—Obtuse in simple leaves, in ternate leaves the terminal is cuneate and side leaflets oblique.

*Leaflet apex.*—Acute.

*Leaflet fragrance.*—Fresh "green" fragrance when crushed.

*Leaflet venation.*—Just slightly reticulate on upper surface, slightly reticulate with prominent main veins on lower surface.

*Leaflet margins.*—Entire.

*Leaflet attachment.*—Petiolutate, slightly articulate.

*Leaflet surface.*—Upper surface; glabrous, lower surface; glabrous with margins and main veins sparsely hairy.

*Leaflet size.*—Up to 8 cm in length and up to 5 cm in width.

*Leaflet color.*—Upper surface 137B to 137C, lower surface 137D.

*Petioles and petiolules.*—Petiole up to 3 cm in length and about 3 mm in width, 147A in color and suffused with 166B, surface sparsely hairy, petiolule; up to 1.2 cm in length and about 2 mm in width, 147A in color and suffused with 166B surface sparsely hairy.

Inflorescence description:

*Inflorescence type.*—Solitary or 3-flowered dichasial cyme.

*Inflorescence arrangement.*—Terminal and axillary on young shoots.

*Peduncles.*—4 to 9 cm in length and an average of 3.5 mm in width, 147B in color with blush of 187A, round and just slightly 6-ribbed in shape, surface is sparsely hairy.

*Pedicels.*—4 to 7 cm in length and an average of 2.5 mm in width, 147B in color with blush of 187A, round in shape, surface sparsely hairy to moderately hairy towards the flower.

*Peduncle bracts.*—Similar to leaf in characteristics but simple.

*Flower bud description.*—Held upright, lanceolate in shape, 144C in color with apex flushed with 187B, apex acuminate, base obtuse, surface sparsely hairy with short hairy seams.

*Flower fragrance.*—None.

*Lastingness of the flowers.*—Individual flowers last up to about 10 days until the first tepal drop followed later by the stamens.

*Flower quantity.*—Solitary flowers or in a 3-flowered dichasial cyme, terminal and axillary on young shoots, about 30 to 40 flowers in spring and 50-70 flowers in summer on a 3 year-old plant.

*Flower type.*—Single, spreading, slightly irregular.

*Flower aspect.*—Upright facing.

*Flower size.*—Range from 6 to 10 cm in diameter and about 3 cm in depth.

*Flower sex.*—Bisexual.

*Tepal number.*—Usually 5 or 6 in number but sometimes 4.

*Tepal shape.*—Elliptic.

*Tepal apex.*—Subacute to acute.

*Tepal base.*—Cuneate.

*Tepal margin.*—Entire, sometimes with an irregular wave.

*Tepal surface.*—Upper surface; glabrous, lower surface; glabrous with main veins sparsely hairy, margin glabrous but very short hairy towards middle.

*Tepal color.*—Upper surface; 86D becoming lighter towards middle and slightly tinted with 144C at base, becoming 97A at the margin to 97C in the middle with base 155A, fading just slightly to 97D; lower surface; 97D to 155A in the center with just a bit of tint 97A, 145D near base.

*Tepal size*.—Up to 5 cm in length and 3.5 cm in width.

Reproductive organs:

*Gynoecium*.—Numerous pistils (about 30 to 40), 1.5 cm in length, style hairy and 156D in color, ovary 145C in color, stigma 155D in color and bit reflexed.

*Androcoecium*.—Filaments are 0.6 to 1.2 cm in length and 1 mm in width, linear, 155B in color and glabrous surface, anthers; 4 mm in length, linear, 158B in color with pollen 158A in color; connective just a bit elongated, 18D in color with a 200B tip later.

*Seed*.—Head 3 to 4 cm in diameter; style plumose and 156D in color, ovary 145C in color with hairs 155B, stigma 158B in color, bent to hooked; seed; usually sterile, seed is rarely produced but sometimes a few ovaries start to develop with longer styles.

It is claimed:

1. A new and distinct cultivar of *Clematis* plant named 'Zobadol' as herein illustrated and described.

* * * * *